United States Patent [19]

Madrange nee Dermain et al.

[11] 3,934,595

[45] Jan. 27, 1976

[54] LACQUERS AND WAVESETTING LOTIONS CONTAINING METHYL METHACRYLATE-DIMETHYLAMINO-ETHYL METHACRYLATE-OCTADECYL METHACRYLATE TERPOLYMERS

[75] Inventors: Annie Madrange nee Dermain, Saint-Germain-en-Laye; Christos Papantoniou, Epinay-sur-Seine, both of France

[73] Assignee: Societe Anonyme dite: L'Oreal, Paris, France

[22] Filed: Sept. 11, 1972

[21] Appl. No.: 287,845

[30] Foreign Application Priority Data
Sept. 13, 1971 Luxemburg............................ 63896

[52] U.S. Cl. ........ 132/7; 260/29.2 N; 260/29.6 ME; 260/29.6 TA; 260/33.4 R; 260/33.8 R; 260/80.73; 424/DIG. 1; 424/DIG. 2; 424/47; 424/71; 424/81
[51] Int. Cl.² ...................... A61K 7/11; A45D 7/00
[58] Field of Search .... 260/80.73, 29.2 N, 29.6 TA, 260/29.6 ME, 33.4 R, 33.8 R; 424/47, DIG. 1, DIG. 2, 71, 81; 132/7

[56] References Cited
UNITED STATES PATENTS

| | | | |
|---|---|---|---|
| 3,026,250 | 3/1962 | Coyner | 424/71 X |
| 3,144,391 | 8/1964 | Goff | 424/47 |
| 3,219,611 | 11/1965 | Witwer | 260/80.73 X |
| 3,257,281 | 6/1966 | Maeder | 424/47 |
| 3,341,505 | 9/1967 | Gander | 260/80.73 X |
| 3,475,363 | 10/1969 | Gander | 260/80.73 X |

FOREIGN PATENTS OR APPLICATIONS

| | | | |
|---|---|---|---|
| 1,177,425 | 1/1970 | United Kingdom | 260/80.73 |

*Primary Examiner*—Sam Rosen
*Assistant Examiner*—Vera C. Clarke
*Attorney, Agent, or Firm*—Mason, Mason & Albright

[57] ABSTRACT

Copolymers having tertiary amine groups and composed of 16 – 43% methyl methacrylate, 25 – 54% dimethylamino ethyl methacrylate and 12 – 52% octadecyl methacrylate are particularly useful as hair treating resins with conventional carriers and additives. The copolymers can be crosslinked by up to 0.15 by an unsaturated agent to produce preferred copolymers used in wavesetting lotions in amounts of 1 – 3%. Such copolymers can also be partially or wholly quaternized by a quaternizing agent. Those copolymers not crosslinked are particularly useful as hair lacquers, especially in aerosol sprays in amounts of 1 – 4%. The molecular weight for the subject copolymers average 10,000 – 1,500,000 and copolymerization can be effected in a solvent with a catalyst wherein the reaction mixture is heated for about 6 to 24 hours at about 80°C. When applied to the hair, the amount of lotion or lacquer used can be 10 – 100 cc. and the treated hair is rolled. After treatment, the hair holds its shape well and is easy to comb.

8 Claims, No Drawings

LACQUERS AND WAVESETTING LOTIONS CONTAINING METHYL METHACRYLATE-DIMETHYLAMINO-ETHYL METHACRYLATE-OCTADECYL METHACRYLATE TERPOLYMERS

The present invention relates to new cosmetic compositions in the form of lacquers and wavesetting lotions which contain a copolymer possessing tertiary amine groups as the resin.

It has already been proposed to use copolymers possessing such tertiary amine groups in order to prepare lacquers or or wavesetting lotions.

In this field, the use of copolymers, and in particular of bipolymers, obtained by copolymerizing 10 to 90%, but preferably 15 to 90%, of an unsaturated ester possessing a tertiary amine group and 90 to 10%, but preferably 85 to 10%, of another unsaturated monomer, the tertiary amine groups of the copolymers being partially quaternized, have been recommended for producing such lacquers or wavesetting lotions.

It has been found, however, that these wavesetting lotions and lacquers based on such resins do not possess all the cosmetic characteristics which are generally required for such hair lotions and lacquers.

After extensive investigations, the applicants have found, entirely surprisingly, that, in order to obtain excellent lacquers and wavesetting lotions based on copolymers possessing tertiary amine groups, it was necessary to produce these copolymers using well defined proportions of each of the constituent monomers.

In effect, it has been found that on going outside the limits selected by the applications, the cosmetic properties of the lacquers and wavesetting lotions were inferior.

Furthermore, these compositions make it possible to produce films which have an excellent shine and a good affinity for hair, which yields the double advantage of holding the head of hair better and of making it easier to comb, without destroying the copolymer film to any great extent.

In effect, it is well known that combing leads to practically complete removal of the resins used, which fall in the form of a white powder. In the case of the wavesetting lotions according to the invention, combing, as was stated above, is made possible, while the copolymer films can, nevertheless, be easily removed by brushing or by washing with a shampoo of conventional type.

It must be pointed out, moreover, that these lacquers and wavesetting lotions according to the invention make it possible for the hair to have a less greasy appearance and to look healthier. It was also found that the softness of the hair, after it had been dried, was markedly improved.

The subject of the present invention is a cosmetic composition for hair, in the form of lacquers or wavesetting lotions, characterized in that it contains, in a suitable cosmetic vehicle, at least one copolymer possessing tertiary amine groups, resulting from the copolymerization of 43 to 16% by weight of methyl methacrylate, 54 to 25% by weight of dimethylamino-ethyl methacrylate and 12 to 52% by weight of octadecyl methacrylate.

As has been stated above, these proportions of methyl methacrylate, dimethylamino-ethyl methacrylate and octadecyl methacrylate are of great importance if it is desired to obtain a film which possesses all the cosmetic properties mentioned above.

The copolymers according to the invention, which are completely soluble in absolute ethyl alcohol, are more particularly intended for preparing aerosol hair lacquers.

In a variant, the methyl methacrylate, dimethylamino-ethyl methacrylate and octadecyl methacrylate terpolymers can be in a crosslinked form.

In general, this cross-linking is carried out during polymerization, for example by means of a small amount of ethylene glycol dimethacrylate or of any other crosslinking agent with a similar structure.

This quantity of crosslinking agent is generally not greater than 0.15 part of crosslinking agent per 100 parts of monomers.

Ethylene glycol dimethacrylate, which is preferably used as the crosslinking agent, possesses two unsaturated groups which simultaneously take part in the copolymerization in two chains of the copolymer, which has the result of producing crosslinking between the various chains of the copolymer.

These crosslinking bonds between the various chains of a copolymer by means of a molecule of ethylene glycol dimethacrylate can be represented in the following manner:

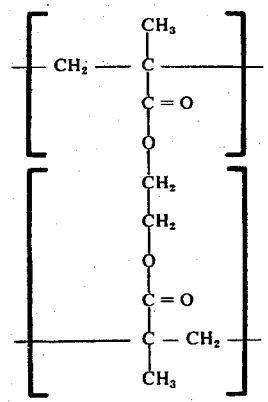

The crosslinked copolymers according to the invention are completely soluble in ethyl alcohol and are more particularly intended for preparing wavesetting lotions, while, on the other hand, the non-crosslinked copolymers are more particularly intended for preparing aerosol lacquers.

The crosslinked copolymers according to the invention can also be partially or completely quaternized, by means of at least one quaternizing agnet. This quaternization can be carried out, for example, by means of agents such as dimethylsulphate and lower alkyl halides such as methyl iodide or ethyl bromide, and 2-bromoethanol, β-propiolactone, 1,3-propane sultone and benzyl chloride, as well as by means of any other quaternizing agent usually employed in this type of reaction.

These crosslinked, quaternized copolymers, which are soluble in diluted alcohols, are more particularly intended for preparing wavesetting lotions, without however excluding the possibility of using them in hair lacquer formulations, especially suited to their solubility.

In general terms, the copolymers used according to the invention have a molecular weight which can be between about 10,000 and 1,500,000.

The wavesetting lotions according to the invention are in the form of aqueous or aqueous-alcoholic solutions which contain 20 to 70% of alcohol, and have a copolymer concentration of between 1 and 3%.

The alcohols which are generally used for producing such wavesetting lotions are preferably lower aliphatic alcohols, of low molecular weight, such as ethanol or isopropanol.

The hair lacquers according to the invention are produced by dissolving at least one copolymer as defined above in an alcohol, this solution being placed in an aerosol vessel and mixed with a propellant gas liquefied under pressure.

It is possible, for example, to produce an aerosol lacquer according to the invention by adding 1 to 4% by weight of at least one copolymer as described above to a mixture consisting of ¼ to ⅓ of an anhydrous aliphatic alcohol such as ethanol or isopropanol and ¾ to ⅔ of a liquefied propellant gas or of a mixture of liquefied propellant gases such as halogenated hydrocarbons of the trichlorofluoromethane or dichlorodifluoromethane type.

Of course, it is possible to add adjuvants, such as plasticizers, perfumes, dyestuffs or any other adjuvant used in cosmetics, to the cosmetic compositions according to the invention.

A further subject of the present invention is a wavesetting process. According to this process, at least one wavesetting lotion as described above is applied to the hair which is then wound up on wavesetting rollers (15 to 30 mm diameter) and the head of hair is dried (temperature of the order of 25° to 55°C.).

The amount to be applied to the hair depends on the volume of the head of hair but is generally of the order of 10 to 100 cc, and preferably of the order of 20 to 50 cc.

The present invention has as a further subject the crosslinked copolymers obtained by copolymerization of 43 to 16% by weight of methyl methacrylate, 54 to 25% by weight of dimethylamino-ethyl methacrylate, 12 to 52% by weight of octadecyl methacrylate and an amount of a crosslinking agent which does not exceed 0.15 part by weight per 100 parts of monomers.

The crosslinking agent is preferably ethylene glycol dimethacrylate, but other crosslinking agents with a similar structure can also be used.

The present invention has as a further subject the crosslinked copolymers mentioned above, the amine groups of which have been quaternized by means of a quaternizing agent.

The copolymers used in the compositions according to the invention are produced according to the conventional process of polymerization, which consists of dissolving the various monomers in a solvent such as absolute ethanol, in the presence of a polymerization catalyst such as alpha,alpha'-azo-bis-isobutyronitrile or alhpa, alpha'-azo-bis-isobutyronitrile hydrochloride and of heating them under nitrogen, while stirring, at a temperature of the order of 80°C.

The duration of heating is generally of the order of 6 to 24 hours.

The polymer is then isolated according to the conventional process.

If it is desired to produce the copolymers in the quaternized form, the quaternization reaction can be carried out in situ by diluting the reaction mixture by adding a sufficient amount of the polymerization solvent and adding the quaternizing agent in the desired amount to produce either partial quaternization or complete quaternization of the tertiary amine groups carried by the dimethylamino-ethyl methacrylate units of the copolymer.

The quaternization reaction is generally exothermic, but, in order to make it go to completion, it is recommended to heat the mixture for a period of the order of 3 to 8 hours, at temperatures of about 50° to 80°C.

In order that the invention shall be better understood, preparation examples of copolymers as well as examples of cosmetic compositions based on these copolymers will now be described, by way of illustration but without implying any limitation.

EXAMPLES OF PREPARATIONS OF POLYMERS

EXAMPLE I 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer. The mixture is stirred until the catalyst has dissolved and 1,080 g of methyl methacrylate, 1,220 g of octadecyl methacrylate, 1,700 g of dimethylamino-ethyl methacrylate and 6 g of ethylene glycol dimethyacrylate are introduced into it.

The mixture is heated to about 80°C. under nitrogen, and with stirring.

The solution gels but the mixture can still be stirred. After heating for 9 hours, the solution is diluted with 2,693 g of absolute ethanol and left to cool to 20°C. 1,360 g of freshly distilled dimethylsulphate are then introduced into it, drop by drop, via the dropping funnel. The temperature of the solution increases rapidly to the reflux temperature of ethanol and remains there until the end of the addition. Heating is then continued for 3 hours at about 80°C. and then the temperature is allowed to fall to 50°C. 1,300 g of solvent are then distilled under reduced pressure (30 mm Hg). Addition of 1,300 g of absolute ethanol and distillation of an equal amount of solvent is repeated three times, and then the solution is diluted with 1,300 g of absolute ethanol. An alcoholic solution of the quaternized crosslinked copolymer is thus obtained, with a yield of the order of 100%.

This copolymer has an average molecular weight of 1,200,000, $(dn/dc) = 0.120$ (solvent AcOH/MeOH = 80/20).

EXAMPLE II

Following the procedure of Example I, copolymerization of 1,624 g of dimethylamino-ethyl methacrylate, 1,712 g of octadecyl methacrylate, 664 g of methyl methacrylate and 6 g of of ethylene glycol dimethacrylate is carried out in 2,667 g of absolute ethyl alcohol, in the presence of 16 g of azo-bis-isobutyronitrile.

At the end of copolymerization, the solution is diluted with 2,638 g of absolute ethyl alcohol and 1,305 g of dimethylsulphate are added so as to quaternize the tertiary amine group of the copolymer.

A quaternized crosslinked copolymer is thus obtained, with an average molecular weight of 1,200,000.

EXAMPLE III

Following the procedure of Example I, copolymerization of 1,204 g of methyl methacrylate, 908 g of octadecyl methacrylate, 1,888 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of polymerization, the solution is diluted with 2,793 g of absolute ethyl alcohol and 1,460 g of methyl methacrylate, 908 g of octadecyl methacrylate, 1,888 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of polymerization, the solution is diluted with 2,793 g of absolute ethyl alcohol and 1,460 g of dimethylsulphate are added in order to quaternize the tertiary amine groups of the dimethylamino-ethyl methacrylate units of the copolymer, to the extent of 100%.

A quaternized crosslinked copolymer is thus obtained, with an average molecular weight of 1,100,000.

EXAMPLE IV

Following the procedure of Example I, copolymerization of 1,368 g of methyl methacrylate, 488 g of octadecyl methacrylate, 2,144 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of copolymerization, the solution is diluted with 3,058 g of absolute ethyl alcohol and 1,725 g of dimethylsulphate are added in order to quaternize the tertiary amine groups of the dimethylamino-ethyl methacrylate units of the copolymer, to the extent of 100%.

A quaternized crosslinked copolymer is thus obtained, with an average molecular weight of 1,300,000.

EXAMPLE V

Following the procedure of Example I, copolymerization of 1,704 g of methyl methacrylate, 504 g of octadecyl methacrylate, 1,792 g of dimethylamino-ethyl methacrylate and 6 g of ethylene glycol dimethacrylate is carried out in 2,667 g of absolute ethanol, in the presence of 16 g of azo-bis-isobutyronitrile.

At the end of the operation, the solution is diluted with 2,771 g of absolute ethyl alcohol and 1,438 g of dimethylsulphate are added in order to quaternize the tertiary amine amine groups of the dimethylamino-ethyl methacrylate units of the copolymer to the extent of 100%.

A quaternized crosslinked copolymer is thus obtained, with an average molecular weight of 1,500,000.

EXAMPLE VI

Following the procedure of Example I, copolymerization of 1,548 g of methyl methacrylate, 872 g of octadecyl methacrylate, 1,580 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of the operation, the solution is diluted with 2,603 g of absolute ethyl alcohol and 1,270 g of dimethylsulphate are added in order to quaternize the tertiary amine groups of the dimethylamino-ethyl methacrylate units of the copolymer, to the extent of 100%.

A quaternized crosslinked copolymer is thus obtained, with an average molecular weight of 1,400,000.

EXAMPLE VII

Following the procedure of Example I, copolymerization of 984 g of methyl methacrylate, 1,968 g of octadecyl methacrylate, 1,048 g of dimethylamino-ethyl methacrylate and 6 g of ethylene glycol dimethacrylate is carried out in 2,667 g of absolute ethyl alcohol, in the presence of 16 g of azo-bis-isobutyronitrile.

At the end of the operation, the solution is diluted with 2,178 g of absolute ethyl alcohol and 845 g of dimethylsulphate are added in order to quaternize the tertiary amine groups of the dimethylamino-ethyl methacrylate units of the copolymer, to the extent of 100%.

A quaternized crosslinked copolymer is thus obtained, with an average molecular weight of 1,000,000.

EXAMPLE VIII

A terpolymer according to the invention is prepared by following the procedure as stated in Example I above up to the quaternization stage. The terpolymer (400 g) is then quaternized, not with dimethylsulphate, but with 135 g of 2-bromo-ethanol, carrying out the reaction at a temperature of 80°C. for 4 hours.

A polymer with a degree of quaternization of 47% is obtained.

Its average molecular weight is 1,000,000.

EXAMPLE IX

The procedure given in Example VIII is followed, using 96 g of ethyl bromide instead of 2-bromo-ethanol, and carrying out the reaction at about 50°C. for 4 hours.

The polymer obtained, which has a degree of quaternization of 75%, has an average molecular weight of 1,100,000.

EXAMPLE X

The procedure given in Example VIII is followed, using 78 g of β-propiolactone as the quaternizing agent, and carrying out the reaction at 80°C. for 4 hours.

The polymer obtained is quaternized to the extent of 100% and it has an average molecular weight of 1,050,000.

EXAMPLE XI

Following the procedure given in Example VIII, a first quaternization is carried out with 70 g of 2-bromo-ethanol, carrying out the reaction for 4 hours at 80°C. which enables a polymer with a degree of quaternization of 25% to be obtained.

This polymer is subjected to a second quaternization using 55 g of 1,3-propane-sultone, also for 4 hours at 80°C. which gives an additional degree of quaternization of 50%.

The polymer thus obtained, which is quaternized to the extent of 75% (25% by 2-bromo-ethanol and 50% by 1,3-propane-sultone has an average molecular weight of 1,100,000.

EXAMPLE XII

Following the procedure given in Example VIII, a first quaternization is carried out using 160 g of ethyl bromide and carrying out the reaction at 60°C. for 7 hours, after which a second quaternization is carried out with 190 g of dimethylsulphate carrying out the reaction for 4 hours at 80°C.

The polymer thus obtained is quaternized to the extent of 100% (46% by ethyl bromide and 54% by dimethylsulphate). It has an average molecular weight of 1,200,000.

EXAMPLE XIII

Following the procedure given in Example VIII, a first quaternization is carried out using 160 g of 2-bromo-ethanol, carrying out the reaction for 7½ hours at 80°C. followed by a second quaternization using 26.6 g of dimethylsulphate, carrying out the reaction for 4 hours at 80°C.

The polymer obtained has a degree of quaternization of 100% (85% by 2-bromo-ethanol and 15% by dimethylsulphate). It has an average molecular weight of 1,200,000.

EXAMPLE XIV

Following the procedure given in Example VIII, quaternization is first carried out using 138 g of benzyl chloride, for 4 hours at 80°C. followed by a second quaternization using 79 g of dimethylsulphate, carrying out the reaction for 4 hours at about 80°C.

The polymer obtained is quaternized to the extent of 100% (42% of benzyl chloride and 58% by dimethylsulphate). It has an average molecular weight of 1,200,000.

EXAMPLE XV 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer. The mixture is stirred until the catalyst has dissolved and 1,080 g of methyl methacrylate, 1,220 g of octadecyl methacrylate, 1,700 g of dimethylamino-ethyl methacrylate and 6 g of ethylene glycol dimethacrylate are introduced into it.

The mixture is heated at about 80°C. under nitrogen and with stirring.

The solution gels but the mixture can still be stirred. After heating for 9 hours, the solution is diluted with 2,693 g of absolute ethanol and left to cool to 20°C. The terpolymer is then precipitated by adding petroleum ether.

A terpolymer with an average molecular weight of 900,000 is thus obtained.

EXAMPLE XVI 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer.

The mixture is stirred until the catalyst has dissolved and 1,624 g of dimethylamino-ethyl methacrylate, 1,712 g of octadecyl methacrylate, 664 g of methyl methacrylate and 6 g of ethylene glycol dimethacrylate are introduced into it.

The mixture is heated at a temperature of about 80°C. under nitrogen and with stirring.

The solution gels but the mixture can still be stirred. After heating for 9 hours, the solution is diluted with 2,693 g of absolute ethanol and is left to cool to 20°C.

The polymer obtained is purified by precipitation in petroleum ether.

It has an average molecular weight of 900,000.

EXAMPLES XVII

Following the procedure given in Example XVI, copolymerization of 1,204 g of methyl methacrylate, 908 g of octadecyl methacrylate, 1,888 g of dimethylamino-ethyl methacrylate and 6 g of ethylene glycol dimethacrylate is carried out.

The polymer obtained has an average molecular weight of 800,000.

XVIII

Following the method of preparation described in Example XVI, copolymerization of 1,368 g of methyl methacrylate, 488 g of octadecyl methacrylate, 2,144 g of dimethylamino-ethyl methacrylate and 6 g of ethylene glycol dimethacrylate is carried out.

A polymer which has an average molecular weight of 900,000 is obtained.

EXAMPLE XIX

Following the procedure given in Example XVI, copolymerization of 1,704 g of methyl methacrylate, 504 g of octadecyl methacrylate, 1,792 g of dimethylamino-ethyl methacrylate and 6 g of ethylene glycol dimethacrylate is carried out. A copolymer with an average molecular weight of 1,100,000 is obtained.

EXAMPLE XX

Following the procedure given in Example XVI, copolymerization of 1,548 g of methyl methacrylate, 872 g of octadecyl methacrylate, 1,580 g of dimethylamino-ethyl methacrylate and 6 g of ethylene glycol dimethacrylate is carried out.

A copolymer which has an average molecular weight of 1,050,000 is obtained.

EXAMPLE XXI

Following the procedure of Example XVI, copolymerization of 984 g of methyl methacrylate, 1,968 g of octadecyl methacrylate, 1,048 g of dimethylamino-ethyl methacrylate and 6 g of ethylene glycol dimethacrylate is carried out.

A polymer with an average molecular weight of 850,000 is obtained.

EXAMPLE XXII 81.66 g of methyl methacrylate, 90 g of octadecyl methacrylate, 128.34 g of dimethylamino-ethyl methacrylate, 1,200 g of absolute ethanol and 6 g of azo-bis-isobutyronitrile are introduced into a 2 liter flask, equipped with a mechanical stirrer, a condenser which can also be used as a distillation column, a nitrogen inlet, a dropping funnel and a thermometer.

The solution is stirred under nitrogen for 24 hours at a temperature of 80°C. and the polymer is left to cool; the polymer precipitates in petroleum ether in the form of a white powder.

The polymer obtained has an average molecular weight, M.W. = 15,000, $(dn/dc) = 0.109$.

Solvent: dioxane/methanol in the ratio 65/35

EXAMPLE XXII 2,667 g of absolute ethanol and 16 g of azo-bis-isobutyronitrile are introduced into a 20 liter flask, equipped with a mechanical stirrer, a condenser which can also be used as a distillation column, a nitrogen inlet, a dropping funnel and a thermometer. The mixture is stirred until the catalyst has dissolved and 1,080 g of methyl methacrylate, 1,220 g of octadecyl methacrylate, 1,700 g of dimethylaminoethyl methacrylate and 3 g of ethylene glycol dimethacrylate are introduced into it.

The mixture is heated at 80°C. under nitrogen and with stirring.

The solution gels but the mixture can still be stirred. After heating for 9 hours, the solution is diluted with 2,693 g of absolute ethanol and left to cool to 20°C. 1,360 g of freshly distilled dimethylsulphate is then introduced into it, drop by drop, via the dropping funnel. The temperature of the solution increases rapidly to the reflux temperature of ethanol and remains there until the end of the addition. Heating is then continued for 3 hours at 80°C. and then the temperature is allowed to fall to 50°C. 1,300 g of solvent are then distilled under reduced pressure (30 mm Hg). Addition of 1,300 g of absolute ethanol and distillation of an equal amount of solvent is repeated three times, and then the solution is diluted with 1,300 g of absolute ethanol. An alcoholic solution of the quaternized crosslinked copolymer is thus obtained, with a yield of the order of 100%.

This copolymer has an average molecular weight of 600,000.

EXAMPLES OF COMPOSITIONS

EXAMPLE 1

A wavesetting lotion for hair is prepared by making up the following mixture:

| | | |
|---|---|---|
| copolymer according to Example I | 2 | g |
| absolute ethyl alcohol | 45 | cc |
| water, q.s.p. | 100 | cc |

Approximately 20 ml of this lotion are applied to hair which has been washed and towelled dry. The hair is then wound up on wavesetting rollers of 15 to 30 mm diameter and then dried by supplying heat externally.

The hair disentangles easily. The lacquering and the shine are excellent.

EXAMPLE 2

A wavesetting lotion for hair is prepared by making up the following mixture:

| | | |
|---|---|---|
| copolymer according to Example II | 3 | g |
| ethyl alcohol | 50 | cc |
| water, q.s.p. | 100 | cc |

After applying this lotion in accordance with the procedure of Example 1, excellent results are obtained, which are particularly outstanding with regard to the shine, the absence of stickiness and the easy of disentangling.

EXAMPLE 3

A wavesetting lotion for hair is prepared by making up the following mixture:

| | | |
|---|---|---|
| copolymer according to Example VI | 1 | g |
| isopropyl alcohol | 40 | cc |
| water, q.s.p. | 100 | cc |

10 to 30 ml of this lotion are applied to hair which has first been washed. The hair is wound up on wavesetting rollers and then dried under a hood at a temperature of 30° to 55°C. An excellent set is thus obtained. The hair is soft and shiny, and the set stays in very well even in the presence of moisture.

EXAMPLE 4

A wavesetting lotion is prepared by making up the following mixture:

| | | |
|---|---|---|
| copolymer according to Example V | 1.5 | g |
| isopropyl alcohol | 60 | cc |
| perfume | 0.2 | g |
| water, q.s.p. | 100 | cc |

Approximately 20 ml of this lotion are applied to hair which has been washed and towelled dry. The hair is then wound up on wavesetting rollers of 15 to 30 mm diameter and is then dried by supplying heat externally.

The hair disentangles easily. The lacquering and the shine are excellent.

EXAMPLE 5

An aerosol lacquer for hair is prepared by making up the following mixture:

| | | |
|---|---|---|
| copolymer according to Example XV | 1.5 | g |
| absolute ethyl alcohol, q.s.p. | 100 | g |

33 g of this solution are then enclosed in an aerosol container in the presence of 66 g of a propellant gas consisting of a mixture of 61.5% of trichlorofluoromethane and 38.5% of dichlorodifluoromethane.

EXAMPLE 6

A lacquer for hair is prepared by making up the following mixture:

| | | |
|---|---|---|
| copolymer according to Example XXII | 2 | g |
| absolute ethyl alcohol, q.s.p. | 100 | g |

33 g of this mixture are placed in an aerosol container in the presence of 66 g of a propellant gas consisting of a mixture of 61.5% of trichlorofluoromethane and 38.5% of dichlorodifluoromethane.

EXAMPLE 7

An aerosol lacquer for hair is prepared by making up the following mixture:

| | | |
|---|---|---|
| copolymer according to Example XXIII | 1.5 | g |
| absolute ethyl alcohol, q.s.p. | 100 | g |

33 g of this solution are introduced into an aerosol container in the presence of 66 g of a propellant gas consisting of a mixture of 61.5% of trichlorofluoromethane and 38.5% of dichlorodifluoromethane.

EXAMPLE 8

A wavesetting lotion for hair is prepared by making up the following mixture:

| | | |
|---|---|---|
| copolymer according to Example XVI | 1 | g |
| isopropyl alcohol | 40 | cc |
| water, q.s.p. | 100 | cc |

10 to 30 ml of this lotion are applied to hair which has first been washed. The hair is wound up on wavesetting rollers and then dried under a hood at a temperature of 30° to 55°C. An excellent set is thus obtained. The hair is soft and shiny and the set stays in very well even in the presence of moisture.

EXAMPLE 9

A wavesetting lotion is prepared by making up the following mixture:

| | | |
|---|---|---|
| copolymer according to Example XX | 1.5 | g |
| isopropyl alcohol | 60 | cc |
| perfume | 0.2 | g |
| water, q.s.p. | 100 | cc |

After applying this lotion in accordance with the procedure of Example 8, excellent results are obtained, which are particularly outstanding with regard to the shine, the absence of stickiness and the ease of disentangling.

EXAMPLE 10

A wavesetting lotion for hair is prepared by making up the following mixture:

| | | |
|---|---|---|
| copolymer according to Example XIII | 3 | g |
| ethyl alcohol | 50 | cc |
| water, q.s.p. | 100 | cc |

This lotion enables hair to be set easily and above all gives it an excellent shine. The hair is soft to the touch and very easy to disentangle. This type of lotion is particularly suitable for sensitive or dry hair.

EXAMPLE 11

A wavesetting lotion for hair is prepared by making up the following mixture:

| | | |
|---|---|---|
| copolymer according to Example VIII | 2 | g |
| absolute ethyl alcohol | 45 | cc |
| water, q.s.p. | 100 | cc |

After applying this lotion in accordance with the procedure of Example 8, excellent results are obtained, which are particularly outstanding with regard to the shine, the absence of stickiness and the ease of disentangling.

EXAMPLE 12

A wavesetting lotion is prepared by making up the following mixture:

| | | |
|---|---|---|
| copolymer according to Example XI | 1.5 | g |
| isopropyl alcohol | 60 | cc |
| perfume | 0.2 | g |
| water, q.s.p. | 100 | cc |

Approximately 20 ml of this lotion are applied to hair which has been washed and towelled dry. The hair is then wound up on wavesetting rollers of 15 to 30 mm diameter and is then dried by supplying heat externally. An excellent set is thus obtained; the hair is soft and shiny and the set stays in very well even in the presence of moisture.

EXAMPLE 13

A wavesetting lotion for hair is prepared by making up the following mixture:

| | | |
|---|---|---|
| copolymer according to Example XIV | 3 | g |
| ethyl alcohol | 50 | cc |
| water, q.s.p. | 100 | cc |

This lotion enables hair to be set very easily and above all gives it an excellent shine. The hair is soft to the touch and very easy to disentangle. This type of lotion is particularly suitable for sensitive of dry hair.

All parts listed herein are by weight unless indicated to the contrary.

What is claimed is:

1. A wave setting lotion composition comprising a solvent selected from the group consisting of water, ethanol, isopropanol and mixtures thereof, 1 to 3% by weight of a copolymer having 16 – 43% by weight of methyl methacrylate, 25 – 54% by weight of dimethylamino-ethyl methacrylate, and 12 – 52% by weight of octadecyl methacrylate, said copolymer having an average molecular weight of about 10,000 to 1,500,000.

2. The composition of claim 1 wherein said copolymer is crosslinked by ethylene glycol dimethacrylate in an amount up to 0.15 parts per 100 parts of monomers in said copolymer.

3. The composition of claim 2 wherein said copolymer is quaternized by a quaternizing agent selected from the group consisting of dimethyl sulfate, a lower alkyl halide having 1 to 3 carbon atoms, 2-bromoethanol, $\beta$-propiolactone 1,3-propane sultone and benzyl chloride.

4. An aerosol hair lacquer composition comprising a mixture of about ¼ to ⅓ by weight of an alcohol selected from the group consisting of ethanol and isopropanol, ⅔ to ¾ by weight of a liquefied propellant gas under pressure and 1 to 4% by weight of a copolymer having 16–43% by weight of methyl methacrylate, 25–54% by weight of dimethylamino-ethyl methacrylate and 12–52% by weight of octadecyl methacrylate, said copolymer having an average molecular weight of about 10,000 to 1,500,000.

5. The composition of claim 4 wherein said copolymer is crosslinked by ethylene glycol dimethacrylate in an amount up to 0.15 parts per 100 parts of monomers in said copolymer.

6. The composition of claim 4 wherein the propellant gas is selected from the group consisting of trichlorofluoromethane, dichlorodifluoromethane and mixtures thereof.

7. The composition of claim 4 wherein said copolymer is quaternized by a quaternizing agent selected from the group consisting of dimethyl sulphate, a lower alkyl halide with 1 to 3 carbon atoms, 2-bromoethanol, $\beta$-propiolactone, 1,3-propane sultone and benzyl chloride.

8. A process for setting hair in waves comprising applying 10–100 cc of a composition having a cosmetic vehicle selected from the group consisting of ethyl alcohol-water, isopropyl alcohol-water and ethyl alcohol-propellant gas and an effective amount of a copolymer possessing tertiary amine groups, said copolymer having an average molecular weight of about 10,000 to 1,500,000 and comprising 16–43% methyl methacrylate, 25–54% dimethylamino-ethyl methacrylate and 12–52% octadecyl methacrylate, winding the hair on curlers and drying the hair.

* * * * *